United States Patent

Schmid et al.

Patent Number: 6,054,454
Date of Patent: Apr. 25, 2000

[54] METHOD OF CONTROLLING FISH PARASITES

[75] Inventors: Hariolf Schmid, Heitersheim, Germany; Ernst Hess, Schönenbuch, Switzerland

[73] Assignee: Novartis Corporation, New York, N.Y.

[21] Appl. No.: 09/068,827

[22] PCT Filed: Nov. 29, 1996

[86] PCT No.: PCT/EP96/05302

§ 371 Date: May 18, 1999

§ 102(e) Date: May 18, 1999

[87] PCT Pub. No.: WO97/21350

PCT Pub. Date: Jun. 19, 1997

[30] Foreign Application Priority Data

Dec. 11, 1995 [CH] Switzerland ............... 3494/95

[51] Int. Cl.$^7$ .......................... A01N 47/40; A01N 51/00
[52] U.S. Cl. ...................... 514/229.2; 514/222.5; 514/223.8; 514/227.2; 514/227.8
[58] Field of Search ............. 514/229.2, 222.5, 514/223.8, 227.2, 227.8; 544/67

[56] References Cited

U.S. PATENT DOCUMENTS 5,504,081 4/1996 Löhr et al. ............... 514/225

FOREIGN PATENT DOCUMENTS 2 100 924 1/1994 Canada .

Primary Examiner—Richard L. Raymond
Attorney, Agent, or Firm—Michael P. Morris

[57] ABSTRACT

The present invention relates to the use of compounds of formula

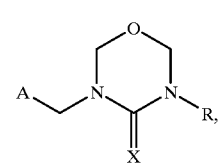

(I)

wherein

A is an unsubstituted or mono- to tetrasubstituted, aromatic or non-aromatic, monocyclic or bicyclic heterocyclic radical, where one to two of the substituents of A can be selected from the group consisting of halo-$C_1$–$C_3$alkyl, cyclopropyl, halocyclopropyl, $C_2$–$C_3$alkenyl, $C_2$–$C_3$alkynyl, halo-$C_2$–$C_3$alkenyl, halo-$C_2$–$C_3$alkynyl, halo-$C_1$–$C_3$alkoxy, $C_1$–$C_3$alkylthio, halo-$C_1$–$C_3$alkylthio, allyloxy, propargyloxy, allylthio, propargylthio, haloallyloxy, haloallylthio, cyano and nitro, and one to four of the substituents of A can be selected from the group consisting of $C_1$–$C_3$alkyl, $C_1$–$C_3$alkoxy and halogen; R is hydrogen, $C_1$–$C_6$alkyl, phenyl-$C_1$–$C_4$alkyl, $C_3$–$C_6$cycloalkyl, $C_2$–$C_6$alkenyl or $C_2$–$C_6$alkynyl; and X is N—$NO_2$ or N—CN, in the free form or in salt form or, if appropriate, tautomers thereof, in the free form or in salt form, for controlling fish parasites, in particular sea lice.

13 Claims, No Drawings

METHOD OF CONTROLLING FISH PARASITES

This application is a 371 of PCT/EP 96/05302, filed Nov. 29, 1996.

The present invention relates to the use of compounds of formula

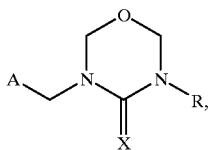

(I)

wherein

A is an unsubstituted or mono- to tetrasubstituted, aromatic or non-aromatic, monocyclic or bicyclic heterocyclic radical, where one to two of the substituents of A can be selected from the group consisting of halo-$C_1$–$C_3$alkyl, cyclopropyl, halocyclopropyl, $C_2$–$C_3$alkenyl, $C_2$–$C_3$alkynyl, halo-$C_2$–$C_3$alkenyl, halo-$C_2$–$C_3$alkynyl, halo-$C_1$–$C_3$alkoxy, $C_1$–$C_3$alkylthio, halo-$C_1$–$C_3$alkylthio, allyloxy, propargyloxy, allylthio, propargylthio, haloallyloxy, haloallylthio, cyano and nitro, and one to four of the substituents of A can be selected from the group consisting of $C_1$–$C_3$alkyl, $C_1$–$C_3$alkoxy and halogen;

R is hydrogen, $C_1$–$C_6$alkyl, phenyl-$C_1$–$C_4$alkyl, $C_3$–$C_6$cycloalkyl, $C_2$–$C_6$alkenyl or $C_2$–$C_6$alkynyl;
and X is N—$NO_2$ or N—CN, in the free form or in salt form or, if appropriate, tautomers thereof, in the free form or in salt form, for controlling fish parasites, in particular sea lice. The invention also relates to a method of controlling these parasites as well as to the use of these compounds or tautomers for the preparation of corresponding antiparasitic compositions.

The compounds of formula I are known and are disclosed, inter alia, in EP-A-0 580 553.

Intensive fish farming sustains substantial economical losses through the injury of fish by parasites. Treatments against these parasites are known; the conventional active substances, however, must be used in relatively high concentrations and require long treatment periods. These active substances therefore cannot fully meet the requirements of a gentle treatment, which is why there is still a need for the provision of further compounds having fish parasite-controlling properties, in particular for controlling fish-parastic crustaceans, which object is achieved according to this invention by the use of compounds I.

Some of the compounds I can exist in the form of tautomers. If, for example, R is hydrogen, then corresponding compounds I, i.e. those having a 3-H-4-imino-perhydro-1,3,5oxadiazine part-structure, can exist in an equilibrium with the relevant tautomers, which have a 4-amino-1,2,5,6-tetrahydro-1,3,5-oxadiazine part-structure. Accordingly, the compounds I hereinabove and hereinafter are, where appropriate, also to be understood as meaning corresponding tautomers, even when no specific mention is made of the latter in each individual case.

Compounds I which have at least one basic centre can form, for example, acid addition salts. These acid addition salts are formed, for example, with strong inorganic acids, such as mineral acids, typically perchloric acid, sulfuric acid, nitric acid, nitrous acid, a phosphoric acid or a hydrohalic acid, with strong organic carboxylic acids, such as unsubstituted or substituted, for example halogen-substituted, $C_1$–$C_4$alkanecarboxylic acids, for example acetic acid, as well as unsaturated or saturated dicarboxylic acids, typically oxalic acid, malonic acid, succinic acid, maleic acid, fumaric acid or phthalic acid, or hydroxycarboxylic acids, for example ascorbic acid, lactic acid, malic acid, tartaric acid or citric acid, or benzoic acid, or with organic sulfonic acids, such as unsubstituted or substituted, for example halogen-substituted, $C_1$–$C_4$alkane- or arylsulfonic acids, typically methane- or p-toluenesulfonic acid. Compounds I which have at least one acidic group can furthermore form salts with bases. Suitable salts with bases are, for example, metal salts such as alkali metal salts or alkaline earth metal salts, typically sodium salts, potassium salts or magnesium salts, or salts with ammonia or with an organic amine, such as morpholine, piperidine, pyrrolidine, a mono-, di- or tri-lower alkylamine, for example ethyl-, diethyl-, triethyl- or dimethylpropylamine, or a mono-, di- or trihydroxy-lower alkylamine, for example mono-, di- or triethanolamine. Moreover, corresponding internal salts may also be formed, where possible. Due to the close relationship between the compounds I in free form and in the form of the salts thereof, the free compounds I, or the salts thereof, are to be understood analogously hereinabove and hereinafter as meaning, if appropriate, also the corresponding salts and the free compounds I, respectively. The same applies to tautomers of compounds I and salts thereof. Generally, the free form is preferrred in each case.

Unless otherwise defined, the general terms used hereinabove and hereinafter have the meanings given below.

Suitable hetero atoms in the basic ring structure of the heterocyclic radical A are all elements of the Periodic Table which can form at least two covalent bonds.

Halogen, as a group per se and as structural element of other groups and compounds, such as haloalkyl, haloalkylthio, haloalkoxy, halocyclopropyl, haloalkenyl, haloalkynyl, haloallyloxy and haloallylthio, is fluoro, chloro, bromo or iodo, preferably fluoro, chloro or bromo, more preferably fluoro or chloro, most preferably chloro.

Carbon-containing groups and compounds contain, unless otherwise defined, in each case 1 up to and including 6, preferably 1 up to and including 2, more preferably 1 or 2, carbon atoms.

Cycloalkyl is cyclopropyl, cyclobutyl, cyclopentyl or cyclohexyl. Cyclopropyl is preferred.

Alkyl, as a group per se and as structural element of other groups and compounds, such as phenylalkyl, haloalkyl, alkoxy, haloalkoxy, alkylthio and haloalkylthio, in each case with due consideration of the number of carbon atoms contained in each case in the particular group or compound, is either straight-chain, i.e. methyl, ethyl, propyl, butyl, pentyl or hexyl, or branched, for example isopropyl, isobutyl, sec-butyl, tert-butyl, isopentyl, neopentyl or isohexyl.

Alkenyl, haloalkenyl, alkynyl and haloalkynyl are straight-chain or branched and contain in each case two or, preferably, one unsaturated carbon-carbon bond(s). The double or triple bonds of these substituents are preferably separated from the remaining part of the compound I by at least one saturated carbon atom. Examples which may be mentioned are allyl, methallyl, but-2-enyl, but-3-enyl, propargyl, but-2-ynyl and but-3-ynyl.

Halogen-substituted carbon-containing groups and compounds, such as haloalkyl, haloalkylthio, haloalkoxy, halocyclopropyl, haloalkenyl, haloalkynyl, haloallyloxy and haloallylthio, can be partially halogenated or perhalogenated, and in the case of a polyhalogenation, the halogen substituents can be identical or different. Typical examples of haloalkyl, as a group per se and as a structural element of other groups and compounds, such as haloalkylthio and haloalkoxy, are methyl which is mono- to trisubstituted by fluoro, chloro and/or bromo, such as $CHF_2$ or $CF_3$; ethyl which is mono- to pentasubstituted by fluoro, chloro and/or bromo, such $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl, each of which is mono- to hepta-substituted by fluoro, chloro and/or bromo, such as $CH_2CHBrCH_2Br$, $CF_2CHFCF_3$, $CH_2CF_2CF_3$, $CF_2CF_2CF_3$ or $CH(CF_3)_2$; and butyl or an isomer therof, each of which can be mono- to nonasubstituted by fluoro, chloro and/ or bromo, such as $CF(CF_3)CHFCF_3$, $CF_2(CF_2)_2CF_3$ or $CH_2(CF_2)_2CF_3$. Typical examples of haloalkenyl are 2,2-difluoroethen-1-yl, 2,2-dichloroethen-1-yl, 2-chloroprop-1-en-3-yl, 2,3-dichloroprop-1-en-3-yl and 2,3-dibromoprop-1-en-3-yl. Typical examples of haloalkynyl are 2-chloroprop-1-in-3-yl, 2,3-dichloroprop-1-in-3-yl and 2,3-dibromoprop-1-in-3-yl. Typical examples of halocyclopropyl are 2-chlorocyclopropyl, 2,2-difluorocyclopropyl and 2-chloro-2-fluorocyclopropyl. Typical examples of haloallyloxy are 2-chloroprop-1-en-3-yloxy, 2,3-dichloroprop-1-en-3-yloxy and 2,3dibromoprop-1-en-3-yloxy. Typical examples of haloallylthio are 2-chloroprop-1-en-3-ylthio, 2,3-dichloroprop-1-en-3-ylthio and 2,3-dibromoprop-1-en-3-ylthio.

In phenylalkyl, an alkyl group bonded to the remainder of the compound I is substituted by a phenyl group, in which case the alkyl group is preferably straight-chained and the phenyl group is preferably bonded in a position higher that α-position, most preferably in ω-position, of the alkyl group; typical examples are benzyl, 2-phenylethyl and 4-phenylbutyl.

Preferred embodiments within the scope of this invention are:

(1) a compound of formula I, wherein A is an unsubstituted or mono- to tetrasubstituted, aromatic or non-aromatic, monocyclic or bicyclic heterocyclic radical, where one or two of the substituents of A can be selected from the group consisting of halo-$C_1$–$C_3$alkyl, cyclopropyl, halocyclopropyl, $C_2$–$C_3$alkenyl, $C_2$–$C_3$alkynyl, halo-$C_2$–$C_3$alkenyl, halo-$C_2$–$C_3$alkynyl, halo-$C_1$–$C_3$alkoxy, $C_1$–$C_3$alkylthio, halo-$C_1$–$C_3$alkylthio, allyloxy, propargyloxy, allylthio, propargylthio, haloallyloxy, haloallylthio, cyano and nitro, and one to four of the substituents of A can be selected from the group consisting of $C_1$–$C_3$alkyl, $C_1$–$C_3$alkoxy and halogen;
R is hydrogen, $C_1$–$C_6$alkyl, $C_3$–$C_6$cycloalkyl, $C_2$–$C_6$alkenyl or $C_2$–$C_6$alkynyl; and
X is N—$NO_2$ or N—CN;

(2) a compound of formula I, wherein the basic ring structure of A is composed of a ring which has 5 to 6 ring members and to which a further ring having 5 or 6 ring members can be fused, and wherein the basic ring structure of A is preferably a ring having 5 or, preferably, 6 ring members;

(3) a compound of formula I, wherein the basic ring structure of A is unsaturated and has, in particular, one double bond or, preferably, 2 to 4, preferably conjugated, double bonds, more preferably 2, preferably conjugated, double bonds, and wherein the basic ring structure preferably has aromatic character;

(4) a compound of formula I, wherein the basic ring structure of A has 1 up to and including 4, in particular 1 up to and including 3, preferably 1 or 2, hetero atoms, particularly preferably 1 hetero atom;

(5) a compound of formula I, wherein the basic ring structure of A is selected from the group consisting of the basic ring structures

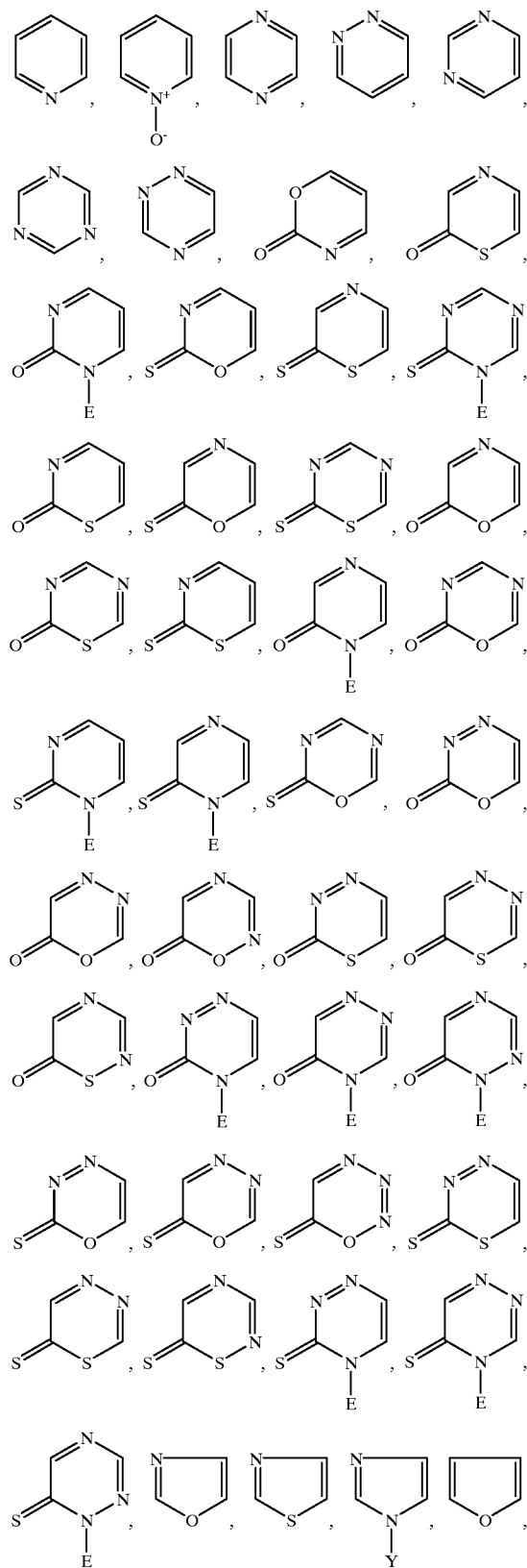

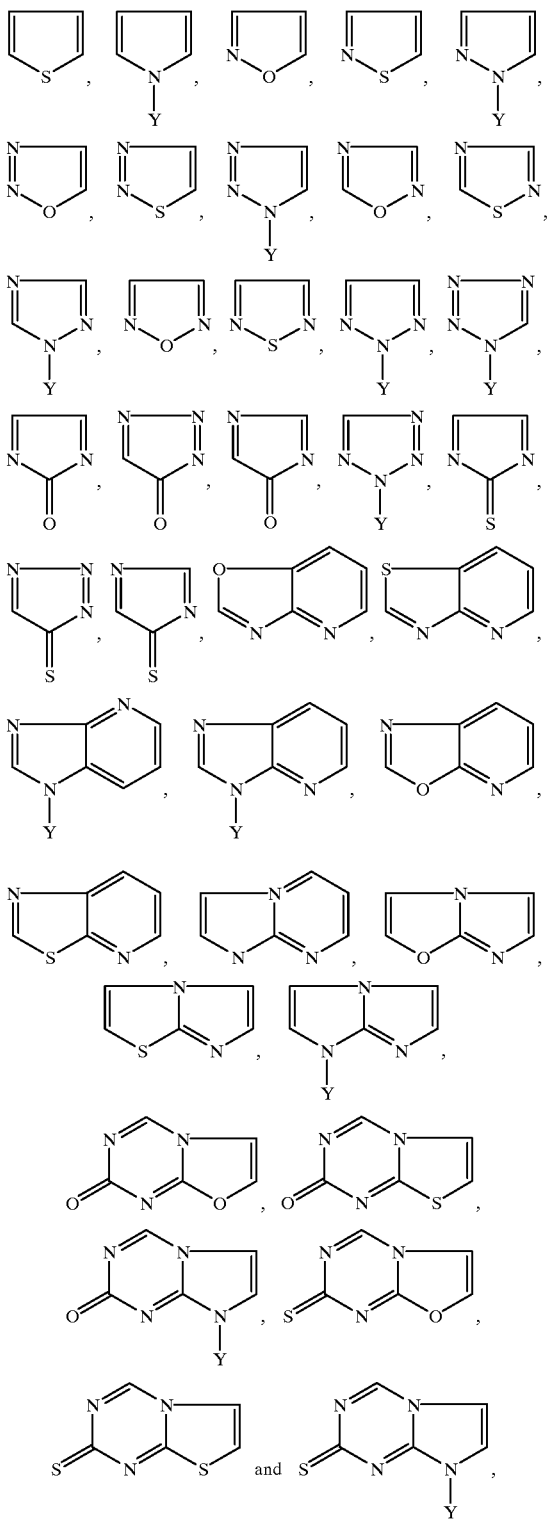

wherein E is in each case $C_1$–$C_3$alkyl, Y is in each case hydrogen, $C_1$–$C_3$alkyl or cyclopropyl, and E and Y, respectively, are not regarded as a substituent of A but considered as part of the basic ring structure of A;

(6) a compound of formula I, wherein the basic ring structure of A contains 1, 2 or 3 hetero atoms selected from the group consisting of oxygen, sulfur and nitrogen, not more than one of the hetero atoms in the basic ring structure being an oxygen atom and not more than one of the hetero atoms in the basic ring structure being a sulfur atom, and wherein the basic ring structure preferably has 1, 2 or 3 hetero atoms selected from the group consisting of oxygen, sulfur and nitrogen, not more than one of the hetero atoms in the basic ring structure being an oxygen or a sulfur atom, and wherein the basic ring structure of A preferably contains at least one nitrogen atom;

(7) a compound of formula I, wherein A is bonded via a C atom of its basic ring structure to the remaining part of the compound I;

(8) a compound of formula I, wherein A is unsubstituted or mono- or disubstituted by substituents selected from the group consisting of halogen, $C_1$–$C_3$alkyl, halo-$C_1$–$C_3$alkyl, $C_1$–$C_3$alkoxy and halo-$C_1$–$C_3$alkoxy, preferably wherein A is unsubstituted or mono- or disubstituted by substituents selected from the group consisting of halogen and $C_1$–$C_3$alkyl;

(9) a compound of formula I, wherein the basic ring structure of A is a pyridyl, 1-oxidopyridinio or thiazolyl group and, preferably, wherein the basic ring structure of A is a pyrid-3-yl, 1-oxido-3-pyridinio or thiazol-5-yl group, more preferably wherein A is a pyrid-3-yl, 2-halopyrid-5-yl, 2,3-dihalopyrid-5-yl, 2-$C_1$–$C_3$alkylpyrid-5-yl, 1-oxido-3-pyridinio, 2-halo-1-oxido-5-pyridinio, 2,3-dihalo-1-oxido-5-pyridinio or 2-halothiazol-5-yl group, even more preferably wherein A is a pyrid-3-yl, 2-halopyrid-5-yl, 2-halo-1-oxido-5-pyridinio or 2-halothiazol-5-yl group, most preferably wherein A is a 2-chloropyrid-5-yl, 2-methylpyrid-5-yl, 1-oxido-3-pyridinio, 2-chlor-1-oxido-5-pyridinio, 2,3-dichloro-1-oxido-5-pyridinio or 2-chlorothiazol-5-yl group, in particular wherein A is a pyrid-3-yl, 2-chloropyrid-5-yl, 2-chloro-1-oxido-5-pyridinio or 2-chlorothiazol-5-yl group, in more particular wherein A is a 2-chloropyrid-5-yl group or, preferably, a 2-chlorothiazol-5-yl group;

(10) a compound of formula I, wherein R is $C_1$–$C_6$alkyl, phenyl-$C_1$–$C_4$alkyl, $C_3$–$C_6$cycloalkyl, $C_3$–$C_4$alkenyl or $C_3$–$C_4$alkynyl, preferably $C_1$–$C_6$alkyl, $C_3$–$C_6$cycloalkyl, $C_3$–$C_4$alkenyl or $C_3$–$C_4$-alkynyl, more preferably $C_1$–$C_6$alkyl, phenyl-$C_1$–$C_4$alkyl, $C_3$–$C_4$alkenyl or $C_3$–$C_4$alkynyl, in particular $C_1$–$C_4$alkyl, most preferably methyl;

(11) a compound of formula I, wherein X is N—$NO_2$;

(12) a compound of formula I, wherein A a pyridyl, 1-oxidopyridinio or thiazolyl group which is bonded via a C atom of its basic ring structure to the remaining part of the compound I and which is unsubstituted or mono- or disubstituted by substituents selected from the group consisting of halogen and $C_1$–$C_3$alkyl; R is $C_1$–$C_6$alkyl, phenyl-$C_1$–$C_4$alkyl, $C_3$–$C_6$cycloalkyl, $C_3$–$C_4$alkenyl or $C_3$–$C_4$alkynyl, and X is N—$NO_2$ or N—CN;

(13) a compound of formula I, wherein A is a 2-chloropyrid-5-yl, 2-methylpyrid-5-yl, 1-oxido-3-pyridinio, 2-chloro-1-oxido-5-pyridinio, 2,3-dichloro-1-oxido-5-pyridinio or 2-chlorothiazol-5-yl group, R is $C_1$–$C_4$alkyl, and X is N—$NO_2$;

(14) a compound of formula I, wherein A is a 2-chlorothiazol-5-yl or 2-chloropyrid-5-yl group, R is $C_1$–$C_4$alkyl, and X is N—$NO_2$.

Specifically preferred compounds within the scope of the invention are (a) 5-(2-chloropyrid-5-ylmethyl)-3-methyl-4-nitroiminoperhydro-1,3,5-oxadiazine, (b) 5-(2-chlorothiazol-5-ylmethyl)-3-methyl-4-nitroiminoperhydro-1,3,5-oxadiazine, (c) 3-methyl-4-nitroimino-5-(1-oxido-3-pyridiniomethyl) perhydro-1,3,5-oxadiazine, (d) 5-(2-chloro-1-oxido-5-pyridiniomethyl)-3-methyl-4-nitroiminoperhydro-1,3,5-oxadiazine, and (e) 3-methyl-5-(2-methylpyrid-5-ylmethyl)-4-nitroiminoperhydro-1,3,5-oxadiazine.

In accordance with this invention the cited compounds are excellently suited for use in the control of fish parasites and, in particular, fish-parasitic crustaceans. These include the Copepodae (cyclops) with the genus Ergasilus
Bromolochus
Chondracaushus
Caligus (−>C. curtus, C. elongatus)
Lepeophtheirus (−>L. salmonis)
Elythrophora
Dichelestinum
Lamproglenz
Hatschekia
Legosphilus
Symphodus
Ceudrolasus
Pseudocycmus
Lernaea
Lernaeocera
Pennella
Achthares
Basanistes
Salmincola
Brachiella
Epibrachiella
Pseudotracheliastes;
and the families
Ergasilidae
Bromolochidae
Chondracanthidae
Calijidae
Dichelestiidae
Philichthyidae
Pseudocycnidae
Lernaeidae
Lernaepotidae
Sphyriidae
Cecropidae, as well as the Branchiuriae (carp lice) with the families Argulidae and the genus Argulus spp.; and also the Cirripediae (barnacles) and *Ceratothoa gandichaugii*.

The fish include useful fish, breeding fish, aquarium fish and toy fish of all ages occurring in freshwater, sea water and brackish water. The useful fish and breeding fish include, for example, carp, eel, trout, whitefish, salmon, bream, roach, rudd, chub, sole, plaice, halibut, Japanese yellowtail (*Seriola quinqueradiata*), Japanese eel (*Anguilla japonica*), red sea bream (*Pagurus major*), sea bass (*Dicentrarchus labrax*), grey mullet (*Mugilus cephalus*), pompano, gilthread seabream (*Sparus auratus*), Tilapia spp., Cichlidae species such as plagioscion, channel catfish.

The compositions of this invention are particularly suitable for treating salmons. The term "salmon" within the scope of this invention will be understood as comprising all representatives of the family Salmonidae, especially of the subfamily salmonini and, preferably, the following species: Salmon salar (Atlantic salmon); Salmon trutta (brown or sea trout); Salmon gairdneri (rainbow trout); and the Pacific salmon (Oncorhynchus): O. gorbuscha; O. keta; O. nekra; O. kisutch, O. tshawytscha and O. mason; also comprised are artificially propagated species such as *Salvelinus spezies* and *Salmo clarkii*.

Preferred objects of the present invention are the Altantic and Pacific salmon and the sea trout.

In present-day salmon and trout farming, juvenile fish are transferred in the smolt stage from fresh-water tanks to sea water cages. These latter are cubic, rectangular or also round cages having a metal frame which is covered with a fairly fine-meshed net. These cages are lowered into the sea until they are 9/10 submerged and then so anchored that they are accessible from the top.

In another variant, the fish are kept in sea water tanks of different shape. The cages are moored in sea inlets such that a constant flow of water passes through them in order to ensure a sufficient supply of oxygen. A constant flow of salt water in the sea water tanks is also maintained along with a supply of oxygen. In this artificial environment the fish are fed and, if necessary, provided with medication until they mature sufficiently for marketing as edible fish or are selected for further breeding.

Extremely intensive cage stocking is maintained in these fish farms. The fish density reaches orders of magnitude of 10 to 25 kg fish/m$^3$. In this pure monoculture, the exceedingly high fish densities coupled with the other stress factors cause the caged fish to become in general markedly more susceptible to disease, epidemics and parasites than their free-living cospecifics. In order to maintain healthy populations, the caged fish must be treated regularly with bactericides and permanently monitored.

Besides infectious diseases, the prime threat in commercial salmon farming is, however, attack by parasites, namely the representatives of the above-mentioned fish-parasitic crustaceans. In particular, two representatives of the class of Copepodae (cyclops) cause substantial losses in yield: Lepeophtheirus (L. salmonis) and Caligus (C. elongatus). These parasites are popularly known as sea lice. They are easily recognised: Lepeophtheirus has a brown, horseshoe-shaped carapace; Caligus is also brown, but much smaller.

These sea lice injure the fish by feeding on the scales, epithelium and the mucosa. When infestation is severe, these parasites also damage underlying dermis. If, moreover, infected salmon ar kept in cooler waters, then they are normally no longer able to protect themselves from these pests. As a consequence, secondary infections and waterlogging will occur, even if the sea lice are removed. In extreme cases, severe wounding resulting from infestation by these parasites leads to further tissue damage caused by ultraviolet radiation or to the death of the fish from osmotic shock or the secondary infections.

Sea lice are meanwhile widely prevalent and encountered in all fish farms. Severe infestation kills the fish. Mortality rates of over 50%, based on sea lice infestation, have been reported from Norwegian fish farms. The extent of the damage depends on the time of year and on environmental factors, for example the salinity of the water and average water temperature. In a first phase, sea lice infestation is seen in the appearance of the parasites attached to the fish and later—even more clearly—from the damage caused to skin and tissue. The most severe damage is observed in smolts which are just in the phase in which they change from fresh water to sea water. The situation is made even worse by the specific conditions in the fish farms, where salmon of different age groups but of the same weight class are kept together; where fouled nets or cages are used; where high salt concentrations are to be found; where flow through the nets and cages is minmal and the fish are kept in a very narrow space.

Fish farmers who are confronted with this parasite problem have to suffer substantial financial losses and to carry additional expense. On the one hand, their fish are debilitated and damaged by the lice, resulting in lower rates of growth increase, and on the the other hand, secondary infections have to be controlled with expensive drugs and labour-intensive measures. The fish can often no longer be sold, as the consumer will reject the damaged fish. This parasitic infestation can pose a threat to the salmon farmer's livelihood.

The worst damage is caused by Lepeophtheirus, as even few parasites cause widespread tissue damage. The life cycle of Lepeophtheirus consists substantially of two free-swimming larval stages (naupilus and copepodid stages), four chalimus stages, one pre-adult stage and the actual adult stage. The chalimus and adult stages are host-dependent.

The most dangerous stages, because they cause the greatest damage, are all those parasiticing on the fish, especially the actual adult stages.

Pest control agents which can be used to combat sea lice are commercially available, for example Trichlorfon (dimethyl-2,2,2-trichloro-1-hydroxyethylphosphonate), which requires concentrations of 300 ppm in sea water, and Dichlorvos (2,2-dichloroethenyldimethyl phosphate), which is effective from a concentration of 1 ppm. The shortcoming of these compounds is, however, the high concentrations in which they have to be used and the ecological problems associated therewith, which are of even greater consequence on account of the high half-life times.

Surprisingly, in the compounds of formula I, a substance has been found which, while having very low toxicity to fish, is even more effective and, in particular, whose photolytic and hydrolytic degradability is more rapid as compared with the known sea lice control agents and, furthermore, which can be successfully used against all pre-adult and adult stages of sea lice on fish.

A further advantageous property of the compounds of formula I is that, at the proposed concentrations, other marine animals such as lobsters, oysters, crustaceans (with the exception of sea lice), fish and marine plants do not suffer injury. Its degradation products are in any case non-injurous to marine fauna and flora.

The fish are either treated orally, e.g via their feed, or by bath treatment, for example in a "medicinal bath" wherein the fish are placed and where they are kept for a period of time (minutes to several hours) e.g. when being transferred from one breeding basin to another. In special cases treatment can also be carried out parenterally, for example by injection. It is also possible to treat the biotope of the fish temporarily or continuously, e.g the net cages, entire ponds, aquaria, tanks or basins in which the fish are kept.

The active substance is administered in formulations which are adjusted to the applications. Formulations for oral administration are, for example, powders, granulates, solutions, emulsifiable concentrates or suspension concentrates which are mixed homogeneously as feed additives with the feed, or powders, granulates, solutions, emulsifiable concentrates or suspension concentrates which are administered in the form of pills, the outer coat of which can consist e.g. of fish feed compositions which cover the active substance completely. Formulations for bath application or for treating the biotope are powders, granulates, solutions, emulsions or suspensions, tablets or the active substance itself. The user may use these formulations in dilute or undilute form.

The active substance in these formulations is used in pure form, as a solid active substance e.g. in a specific particle size or, preferably, together with - at least - one of the adjuvants which are conventionally used in formulation technology, such as extenders, typically solvents or solid carriers, or surface-active compounds (surfactants).

The formulations are prepared in a manner known per se, typically by mixing, granulating and/or compacting the active substance with solid or liquid carriers, where appropriate with the addition of further adjuvants, such as emulsifiable or dispersing agents, solubilisers, colourants, antioxidants and/or preservatives.

In practice it is also possible to use, for example, those forms of application where the active substance is contained in a readily water-soluble matrix of a film, or in films from which it diffuses over the period of application.

The active substance itself, in ground form or in one of the above formulations, can be used in water-soluble packagings, e.g. in polyvinyl alcohol bags which can be used together with the closed packaging. In this case the user in no longer exposed to the active substance or its formulation.

It is also possible to use semi-solid formulations for the bath treatment. The active substance, which is suspended or dissolved in oily or fatty matrices, is washed out. The release can be controlled by the choice of adjuvants, concentration of the active substance and form (surface). Coprimates or melts of hard fats comprising the active substance are also suitable for use.

The diluted compositions of this invention are prepared by contacting the active substance of formula I with liquid and/or solid formulation assistants by stepwise mixing and/or grinding such that an optimal development of the antiparasitic activity of the formulation is achieved which conforms with the application.

The formulation steps can be supplemented by kneading, granulating (granulates) and, if desired, compressing (pills, tablets).

Formulation assistants can be, for example, solid carriers, solvents and, where appropriate, surface-active substances (surfactants) which are non-toxic for marine fauna and flora.

The following formulation assistants can be typically used for preparing the compositions of this invention:

Solid carriers are, for example, kaolin, talcum, bentonite, sodium chloride, calcium phosphate, carbohydrates, cellulose powder, cotton seed meal, polyethylene glycol ether, if necessary binders such as gelatin, soluble cellulose derivatives, if desired with the addition of surface-active compounds such as ionic or nonionic dispersants; also natural mineral fillers such as calcite, montmorillonite or attapulgite. To improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues. The active substance can also be added to sorptive organic materials, such as polyacrylates, and be applied in this form.

Suitable solvents are: aromatic hydrocarbons which may be partially hydrogenated, preferably the fractions containing 8 to 12 carbon atoms, e.g. alkylbenzenes or xylene mixtures, alkylated napthalenes or tetrahydronaphthalenes, aliphatic or cycloaliphatic hydrocarbons such as paraffins or cyclohexane, alcohols such as ethanol, propanol or butanol, glycols and their ethers and esters, such as propylene glycol, dipropylene glycol ether, ethylene glycol or ethylene glycol monomethyl ether or ethylene glycol monoethyl ether, ketones such as cyclohexanone, isophorone or diacetanol alcohol, strongly polar solvents such as N-methyl-2-pyrrolidone, dimethyl sulfoxide or N,N-dimethyl formamide, water, as well as vegetable oils or epoxidised vegetable oils such as epoxidised rape-seed oil, castor oil, coconut oil or soybean oil, and silicone oils.

Depending of the type of formulation, suitable surface-active compounds are nonionic, cationic and/or anionic surfactants having good emulsifying, dispersing and wetting properties. The surfactants indicated hereinafter are only quoted as examples; the relevant literature describes many more surfactants which are conventionally used in formulation technology and which are suitable according to this invention.

Suitable nonionic surfactants are preferably polyglycol ether derivatives of aliphatic or cycloaliphatic alcohols, or saturated or unsaturated fatty acids, and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols. Further suitable nonionic surfactants are the water-soluble polyadducts of polyethylene oxide with polypropylene glycol, ethylenediaminopolypropylene glycol and alkylpolypropylene glycol containing 1 to 10 carbon atoms in the alkyl chain, which polyadducts contain 20 to 250 ethylene glycol ether groups and 10 to 100 propylene glycol ether groups. These compounds usually contain 1 to 5 ethylene glycol units per propylene glycol unit. Illustrative examples of nonionic surfactants are nonylphenol polyethoxyethanols, polyethoxylated castor oil, polyadducts of polypropylene and polyethylene oxide, tributylphenoxy polyethoxyethanol, polyethylene glycol and octylphenoxy polyethoxyethanol. fatty acid esters of polyoxyethylene sorbitan are also suitable nonionic surfactants, typically polyoxyethylene sorbitan trioleate.

Cationic surfactants are preferably quaternary ammonium salts carrying, as substituent, at least one $C_8$–$C_{22}$ alkyl radical and, as further substituents, optionally halogenated lower alkyl, benzyl or hydroxy-lower alkyl radicals. The salts are preferably in the form of halides, methyl sulfates or ethyl sulfates, for example stearyl trimethylammonium chloride or benzyl bis(2-chloroethyl) ethyl ammonium bromide.

Suitable anionic surfactants may be water-soluble soaps as well as water-soluble synthetic surface-active compounds. Suitable soaps are the alkali metal salts, alkaline earth metal salts, ammonium salts or substituted ammonium salts of higher fatty acids ($C_{10}C_{22}$), e.g. the sodium or potassium salts of oleic or stearic acid, or of natural fatty acid mixtures which can be obtained, inter alia, from coconut oil or tallow oil. Further suitable soaps are also the fatty acid methyl taurin salts. More often, however, so-called synthetic surfactants are used, especially fatty alcohol sulfonates, fatty alcohol sulfates, sulfonated benzimidazole derivatives or alkylarylsulfonates. The fatty alcohol sulfonates or sulfates are usually in the form of alkali metal salts, alkaline earth metal salts, ammonium salts or substituted ammonium salts, and they normally contain a $C_8$–$C_{22}$ alkyl radical which also includes the alkyl moiety of acyl radicals, e.g. the sodium or calcium salt of ligninsulfonic acid, or dodecylsulfate, or of a mixture of fatty alcohol sulfates obtained from natural fatty acids. These compounds also comprise the salts of sulfated or sulfonated fatty alcohol/ethylene oxide adducts. The sulfonated benzimidazole derivatives preferably contain two sulfonic acid groups and one fatty acid radical containing 8 to 22 carbon atoms. Illustrative examples of alkylarylsulfonates are the sodium, calcium or triethanolamine salts of dodecylbenzenesulfonic acid, dibutylnaphthalenesulfonic acid, or of a condensate of nathphtalenesulfonic acid and formaldehyde. Corresponding phosphates, typically salts of the phosphoric acid ester of an adduct of p-nonylphenol with 4 to 14 mol of ethylene oxide, or phospholipids, are also suitable.

Suitable binders for water-soluble granulates or tablets are, for example, chemically modified polymeric natural substances which are soluble in water or in alcohol, such as starch, cellulose or protein derivatives (e.g. methyl cellulose, carboxymethyl cellulose, ethylhydroxyethyl cellulose, proteins such as zein, gelatin and the like), as well as synthetic polymers, typicallyl polyvinyl alcohol, polyvinyl pyrrolidone etc. Tablets may also contain, for example, fillers (e.g. starch, microcrystalline cellulose, sugar, lactose etc.), lubricants and disintegrators.

The bath application of the compositions of this invention to the parasites to be controlled can be carried out, for example, such that the composition are placed in the cage in the form of solutions, emulsions, suspensions, powders or tablets, where they are quickly dissolved and dispersed by the movement of the fish and the flow of the water. Concentrated solutions can also be diluted with large volumes of water before being placed into the cages. Concentration problems do not normally occur in the cages because the fish, in expectation of food, move wildly whenever the cages are opened, thereby promoting fast dilution.

The antiparasitic compositions of this invention normally comprise 0.1 to 99%, preferably 0.1 to 95%, of active substance and 1 to 99.9%, preferably 5 to 99.9%, - at least - of a solid or liquid adjuvant, 0 to 25%, preferably 0.1 to 20%, of the composition preferably being surfactants (%=percent by weight). While concentrated compositions are sometimes preferred as commercial goods, the end user, e.g. for bath application, normally uses compositions which are diluted with water and which have a substantially lower active substance content. Such compositions can contain further adjuvants, such as stabilisers, antifoams, viscosity regulators, binders, tackifiers as well as other active substances for achieving special effects. Preferred compositions are, in particular, composed as follows: (%=percent by weight):

Emulsifiable concentrates:
active substance: 1 to 90%, preferably 5 to 20%
surfactant: 1 to 30%, preferably 10 to 20%
solvent: 5 to 98%, preferably 70 to 85%
Suspension concentrates:
active substance: 5 to 75%, preferably 10 to 50%
water: 94 to 24%, preferably 88 to 30%
surfactant: 1 to 40%, preferably 2 to 30%
Wettable powders:
active substance: 0.5 to 90%, preferably 1 to 80%
surfactant: 0.5 to 20%, preferably 1 to 15%
solid carrier: 5 to 99%, preferably 15 to 98%
Granulates:
active substance: 0.5 to 30%, preferably 3 to 15%
solid carrier: 99.5 to 70%, preferably 97 to 85%

The concentration of the active substance during application depends on the manner and duration of treatment and also on the age and condition of the fish so treated. In the case of short-term treatment, for example, it is from 0.1 to 100 mg of active substance per litre of water, preferably from 0.5 to 10 mg per litre, at a treatment duration of e.g. 0.3–4 hours. In the case of pond applications it is possible to use e.g. from 0.01 to 50 mg of active substance per litre of water.

Formulations for application as feed additive are composed e.g. as follows (%=percent by weight):
 a) active substance: 1 to 10% soybean protein: 49 to 90% ground calcium powder: 0 to 50%
 b) active substance: 0.5 to 10% benzyl alcohol: 0.08 to 1.4% hydroxypropylmethyl cellulose: 0 to 3.5% water: ad 100%

Preparation formulations for the bath application are, for example, the following emulsifiable concentrates, solutions, granulates or suspension concentrates:

FORMULATION EXAMPLES (%=percent by weight)

| Example F1: Emulsifiable concentrates | a) | b) | c) |
|---|---|---|---|
| active substance | 25% | 40% | 50% |
| calcium dodecylbenzene sulfonate | 5% | 8% | 6% |
| castor oil polyethylene glycol ether (36 mol EO) | 5% | — | — |
| tributylphenol polyethylene glycol ether (30 mol EO) | — | 12% | 4% |
| cyclohexanone | — | 15% | 20% |
| xylene mixture | 65% | 25% | 20% |

Emulsions of any required concentration can be produced from such concentrates by dilution with water.

| Example F2: Solutions | a) | b) | c) | d) |
|---|---|---|---|---|
| active substance | 80% | 10% | 5% | 95% |
| ethylene glycol monomethyl ether | 20% | — | — | — |
| polyethylene glycol MG 400 | — | 70% | — | — |
| N-methyl-2-pyrrolidone | — | 20% | — | — |
| epoxidised coconut oil | — | — | 1% | 5% |
| benzine (boiling points 160–190° C.) | — | — | 94% | — |

These solutions are suitable for application in the form of microdrops.

| Example F3: Granulates | a) | b) | c) | d) |
|---|---|---|---|---|
| active substance | 5% | 10% | 8% | 21% |
| kaolin | 94% | — | 79% | 54% |
| highly dispersed silicic acid | 1% | — | 13% | 7% |
| attapulgite | — | 90% | — | 18% |

The active substance is dissolved in dichloromethane, the solution is sprayed onto the carrier, and the solvent is subsequently removed by evaporation under vacuum.

| Example F4: Emulsifiable concentrate | |
|---|---|
| active substance | 10% |
| octylphenol polyethylene glycol ether (4-5 mol EO) | 3% |
| calcium dodecylbenzene sulfonate | 3% |
| castor oil polyglycol ether (36 mol EO) | 4% |
| cyclohexanone | 30% |
| xylene mixture | 50% |

Emulsions of any required concentration can be produced from such concentrates by dilution with water.

| Example F5: Extruder granulate | |
|---|---|
| active substance | 10% |
| sodium ligninsulfonate | 2% |
| carboxymethyl cellulose | 1% |
| kaolin | 87% |

The active substance is mixed with the adjuvants and the mixture is ground and moistened with water. This mixture is extruded, granulated and then dried in a stream of air.

| Example F6: Coated granulates | |
|---|---|
| active substance | 3% |
| polyethylene glycol (MG 200) | 3% |
| kaolin | 94% |

The finely ground active substance is uniformly applied, in a mixer, to the kaolin moistened with polyethylene glycol. Non-dusty coated granulates are obtained in this manner.

| Example F7: Suspension concentrate | |
|---|---|
| active substance | 40% |
| ethylene glycol | 10% |
| nonylphenol polyethylene glycol ether (15 mol EO) | 6% |
| sodium ligninsulfonate | 10% |
| carboxymethyl cellulose | 1% |
| 37% aqueous formaldehyde solution | 0.2% |
| silicone oil in the form of a 75% aqueous emulsion | 0.8% |
| water | 32% |

The finely ground active substance is homogeneously mixed with the adjuvants, giving a suspension concentrate from which suspensions of any desired concentration can be obtained by dilution with water.

Biological Examples

1. Toxicity to salmon lice (in vitro test)

a) Collecting and cultivating the salmon lice

Adult and pre-adult stages of the salmon louse are gently removed with broad forceps from naturally infected Atlantic salmon which have been kept in fish farms, separated according to stage and sex, and kept in sea water tanks at 10° C. and under continuous aeration. The sea water used for cultivating the lice comes from the fish farm from which the infected salmon have been taken. The tests themselves are carried out over 48 hours after collecting the lice.

b) In vivo test for determining the contact action of the control agent

Plastic containers are filled with 50 ml of sea water (10° C.). Into each container are put 5 female and 5 male adults as well as 5 pre-adult salmon lice. The water is rapidly decanted through a sieve and replaced by 50 ml of the test solution (sea water of 10° C., containing the test compound). The lice are treated in this solution for 1 hour, as this corresponds more or less to the conditions in the fish cages. Each container is then flushed with fresh sea water and the lice are kept in fresh sea water. The test is evaluated by making a mortality count of the lice in accordance with sex, stage and concentration of test compound. The count is repeated hourly until there are no more lice surviving. All tests are carried out in triplicate.

b1) Range-finding test

The lice are treated according to b) with active substance concentrations of 0.001 to 1.0 ppm for a period of 1 hour, and the mortality rate is determined by counting the dead parasites.

Compounds of formula I show good activity in this test.

b2) Effect of temperature and salinity on the toxicity of the active substance

The effect of temperature is determined at values from 4° C. to 16° C. at an active substance concentration of 0.01 ppm and a treatment time of 1 hour.

Compounds of formula I show good activity in this test.

2. Toxicity against salmon lice (in vivo test)

Five naturally infected Atlantic salmon are taken from the cage and transferred to well aerated sea water tanks. They remain there for 48 hours for acclimatisation, and feed is withheld for 24 hours before the addition of test compound. A group of 5 salmon is treated at a concentration of 1.0 ppm of test compound, and a second group of 5 salmon is treated at a concentration of 0.1 ppm. The fish are kept for 24 hours in fresh sea water (without test compound) and a count is then made of dead and still living parasites. An untreated group of fish is also included in the evaluation. The test is carried out in triplicate.

Compounds of formula I show good activty in this test.

What is claimed is:

1. A method of controlling fish parasites which comprises treating the parasites with an effective antiparasitic amount of at least one compound of the formula

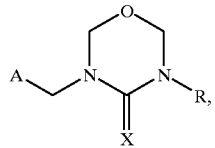

(I)

wherein

A is an unsubstituted or mono- to tetrasubstituted, aromatic or non-aromatic, monocyclic or bicyclic heterocyclic radical, where of the substituents of A when it is mono- or disubstituted are selected from the group consisting of halo-$C_1$–$C_3$alkyl, cyclopropyl, halocyclopropyl, $C_2$–$C_3$alkenyl, $C_2$–$C_3$alkynyl, halo-$C_2$–$C_3$alkenyl, halo-$C_2$–$C_3$alkynyl, halo-$C_1$–$C_3$alkoxy, $C_1$–$C_3$alkylthio, halo-$C_1$–$C_3$alkylthio, allyloxy, propargyloxy, allylthio, propargylthio, haloallyloxy, haloallylthio, cyano and nitro, and the substituents of A when it is mono- to tetrasubstituted are selected from the group consisting of $C_1$–$C_3$alkyl, $C_1$–$C_3$alkoxy and halogen;

R is hydrogen, $C_1$–$C_6$alkyl, phenyl-$C_1$–$C_4$alkyl, $C_3$–$C_6$cycloalkyl, $C_2$–$C_6$alkenyl or $C_2$–$C_6$alkynyl; and X is N—$NO_2$ or N—CN in the free form or in salt form.

2. A method according to claim 1, wherein the active substance concentration is 0.005 to 2 ppm.

3. A method according to claim 1, wherein the active substance is dissolved in the ambient water of the parasite.

4. A method according to claim 1, wherein the active substance is dissolved in dilute form in the ambient water of the parasite.

5. A method according to claim 1, wherein the active substance is added to the feed provided to the fish.

6. A method according to claim 5, which comprises offering the active substance to the fish in the form of pills, the outer coat of which can consist of fish feed compositions which cover the active substance completely.

7. A method according to claim 1, which is used in commercial salmon and trout production.

8. The method according to claim 1 wherein the parasites infest fish of the Salmonidae family.

9. The method according to claim 8 wherein the fish are selected from the group consisting of *Salmon salar, Salmon trutta, Salmon gairdneri, Oncorhynchus gorbuscha, Oncorhynchus keta, Oncorhynchus nekra, Oncorhynchus kisutch, Oncorhynchus tshawytscha, Oncorhynchus mamson, Salvelinus spezies* and *Salmo clarkii*.

10. The method according to claim 1 wherein the parasites are of the Copepodae class.

11. The method according to claim 10 wherein the parasites are of the Lepeophtheirus or Caligus species.

12. The method according to claim 11 wherein the parasites are *Lepeophtheirus salmonis* or *Caligus elongatus*.

13. The method according to claim 1 wherein A is 2-chiorothiazol-5-yl, R is methyl, and X is N—$NO_2$.

* * * * *